(12) United States Patent
Zeik et al.

(10) Patent No.: US 9,171,649 B2
(45) Date of Patent: *Oct. 27, 2015

(54) SHIELDED STRUCTURE FOR RADIATION TREATMENT EQUIPMENT AND METHOD OF ASSEMBLY

(75) Inventors: Gary Zeik, Plantation, FL (US); Eric Landau, Palm Beach, FL (US); Joe Don Garrison, Indianapolis, IN (US); Cheri Ann Oquist, Pembroke Pines, FL (US); Ronald C. McCarthy, Westwood, MA (US); Theodore M. Englehart, Indianapolis, IN (US)

(73) Assignee: Rad Technology Medical Systems LLC, Aventura, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/710,638

(22) Filed: Feb. 23, 2010

(65) Prior Publication Data
US 2010/0146870 A1 Jun. 17, 2010

Related U.S. Application Data

(63) Continuation of application No. 11/301,036, filed on Dec. 12, 2005, now Pat. No. 7,665,249, which is a continuation of application No. 09/854,970, filed on May 14, 2001, now Pat. No. 6,973,758.

(51) Int. Cl.
| | |
|---|---|
| *E04B 1/348* | (2006.01) |
| *E04H 1/12* | (2006.01) |
| *E04H 3/00* | (2006.01) |
| *A61N 5/10* | (2006.01) |
| *G21F 3/04* | (2006.01) |
| *E04H 3/08* | (2006.01) |

(52) U.S. Cl.
CPC ............... *G21F 3/04* (2013.01); *E04B 1/3483* (2013.01); *E04H 1/1205* (2013.01); *E04H 1/125* (2013.01); *E04H 1/1277* (2013.01); *E04H 3/08* (2013.01); *A61N 5/10* (2013.01); *A61N 2005/1094* (2013.01)

(58) Field of Classification Search
CPC ......... E04H 1/00; E04H 1/1205; E04H 1/125; E04H 1/1283; E04H 1/1277; E04H 1/005; E04H 3/08; E04B 1/00; E04B 1/3483; A61N 2005/1094
USPC .................. 588/16, 249, 259; 52/79.1, 79.11, 52/79.12, 561
See application file for complete search history.

(56) References Cited

U.S. PATENT DOCUMENTS

| | | | | |
|---|---|---|---|---|
| 4,433,522 | A * | 2/1984 | Yerushalmi | 52/426 |
| 5,511,908 | A * | 4/1996 | Van Valkenburgh et al. | 405/129.55 |
| 5,695,443 | A * | 12/1997 | Brent et al. | 588/249 |
| 5,727,353 | A * | 3/1998 | Getz et al. | 52/79.1 |
| 5,735,639 | A * | 4/1998 | Payne et al. | 405/129.57 |
| 6,155,747 | A * | 12/2000 | Payne et al. | 405/129.55 |
| 6,372,157 | B1 * | 4/2002 | Krill et al. | 252/478 |

* cited by examiner

*Primary Examiner* — Jessica Laux
(74) *Attorney, Agent, or Firm* — Overhauser Law Offices LLC (57) ABSTRACT

A modularized approach for rapidly and cost effectively assembling a structure suitable for housing radiation emitting equipment is disclosed. The modules include reinforced walls to contain radiation shielding fill material. The modules are transported empty and then filled on site with the fill material to form a radiation shielding barrier around radiation emitting equipment.

5 Claims, 12 Drawing Sheets

SHIELDED STRUCTURE FOR RADIATION TREATMENT EQUIPMENT AND METHOD OF ASSEMBLY

RELATED APPLICATION DATA

This application is a continuation of U.S. application Ser. No. 11/301,036 filed Dec. 12, 2005, now U.S. Pat. No. 7,665,249, which is a continuation of U.S. application Ser. No. 09/854,970 filed May 14, 2001, now U.S. Pat. No. 6,973,758, the disclosures of which are hereby incorporated by reference.

BACKGROUND

The present invention relates generally to structures and portions thereof for housing radiation emitting equipment and shielding humans working near the equipment. More particularly but not exclusively the present invention relates to a modularized approach for rapidly and cost effectively assembling a structure suitable for housing radiation emitting equipment. In a preferred embodiment, the structure may be used in medical applications.

Radiation is used in the diagnosis and treatment of patients in various ways. However, while controlled doses can be beneficial to a patient, those working with the radiation or merely in the surrounding area need to be protected from the harmful effects of the radiation. Accordingly, shielding is traditionally provided to isolate the radiation source from those in the surrounding area and provide some protection from the levels associated with normal use of the equipment and also, to some extent, to accidents with the radiation equipment.

However, the need for shielding, which is traditionally provided by concrete walls or mounds of dirt, severely limits the feasibility of radiation treatment centers in many locations. This limitation is due at least in part to the high cost of constructing these buildings and to the inability to easily disassemble or remodel the centers to accommodate new development of the surrounding structures and land. Accordingly, new apparata and techniques are needed for rapidly and economically constructing radiation treatment centers to allow facilities to be located wherever patients needs require such facilities. Various embodiments of the present invention address these and other needs.

SUMMARY

The present invention provides systems and techniques for rapidly and cost effectively assembling structures for radiation emitting equipment. While the actual nature of the invention covered herein can only be determined with reference to the claims appended hereto, certain aspects of the invention that are characteristic of the embodiments disclosed herein are described briefly as follows.

In one aspect, a system for housing radiation emitting equipment comprises: a plurality of modules that are connected to form an interior area and a barrier substantially surrounding the interior area. The interior area is adapted for human occupation and to contain radiation emitting equipment, and the modules comprise a support frame structure and at least one wall, wherein the support frame structure is horizontally elongated and permits the module to be free standing. The barrier includes first and second spaced apart rigid walls and a quantity of radiation shielding filler material contained between the first and second walls. The quantity of filler material is sufficient to substantially reduce the measurable radiation level outside the interior area when radiation is emitted from the radiation emitting equipment. In one refinement of this system at least two of the plurality of modules each include portions of said first and second spaced apart rigid walls, the portions defining a channel comprising a portion of the barrier. In another refinement, radiation shielding plates are mounted to the support frame structure at selected locations to provide additional radiation shielding. In a still further refinement, a second plurality of modules are connected to form a roof over the interior area, the roof including a roof barrier above the interior area comprising a rigid floor supporting a quantity of radiation shielding filler material above the interior area. In another refinement, the interior area comprises a portion of at least one module that includes a frame structure for supporting the radiation emitting equipment.

In another aspect, a method of constructing a structure for housing radiation emitting equipment comprises: transporting a plurality of modules to a site; positioning the modules adjacent each other with a major axis of each module horizontal; connecting adjacent modules; forming a channel spanning adjacent modules; pouring radiation shielding filler material into the channel to form a barrier; and providing radiation emitting equipment in a central area bordered by the barrier; wherein the quantity of filler material is sufficient to substantially reduce the measurable level of radiation outside the central area when radiation is emitted by the equipment in the central area. In one refinement, the modules each have a long side and a short side and connecting adjacent modules involves connecting their long sides together. In another refinement, a floor structure is formed over the central area; and radiation shielding filler material is poured onto the floor structure.

In another aspect, a method for constructing a structure housing radiation emitting equipment comprises: providing a piece of radiation emitting equipment; providing a free standing frame structure; supporting spaced apart rigid walls with the frame structure to form a channel open at the bottom of the frame structure and laterally spaced from the radiation emitting equipment; and pouring a sufficient amount of a granular fill material into the channel to form a radiation barrier to protect persons on one side of the barrier from the harmful effects of the radiation emitted by the radiation emitting equipment on the other side of the barrier. In one refinement, a plurality of free standing frame structures are provided and the channel spans between frame structures. In another refinement, a support frame structure is provided attached to the free standing frame structure; and the radiation emitting equipment is supported on the support frame structure. In a still further refinement, a direction is selected relative to the radiation emitting equipment; and radiation shielding plates are attached to the free standing frame structure to provide additional shielding in the selected direction.

In another aspect, a method comprises: providing a transportable module for forming a structure, the module comprising: a free standing frame structure, a pair of spaced apart reinforced rigid walls mounted to the frame and defining a channel space between the walls, wherein at least a portion of the channel space between the walls does not contain a ceiling or a floor, lifting the module by its ends; placing the module on a foundation with a major axis of the module horizontal; and filling the channel space with a radiation shielding granular fill, the granular fill contacting the foundation to form a substantially continuous lateral barrier to protect persons on a first side of the channel space from radiation emitted by a piece of radiation emitting equipment on a second opposing side of the channel space. In one refinement, lateral forces acting from inside the channel to force the walls apart are resisted with rigid supports connected in the channel space between the walls. In another refinement, a piece of therapeutic radiation emitting equipment is provided on the second side of the channel space, and a human on the second side is subjected to therapeutic radiation doses with the therapeutic radiation emitting equipment. In a still further refinement, a plurality of modules are provided.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated structures and methods, and such further applications of the principles of the invention as illustrated therein being contemplated as would normally occur to one skilled in the art to which the invention relates.

Figure 1:
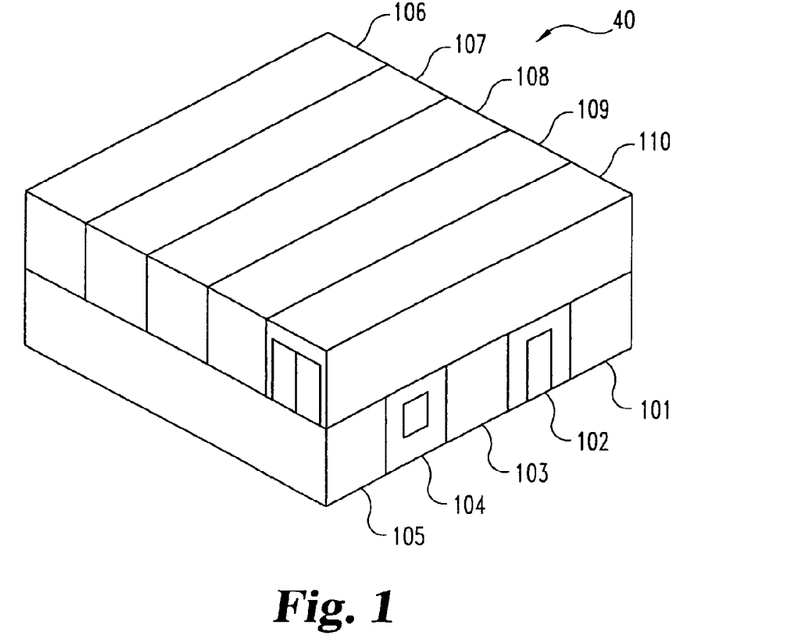
FIG. 1 is a perspective view of an assembled modular structure according to one embodiment of the present invention.
Figure 2:
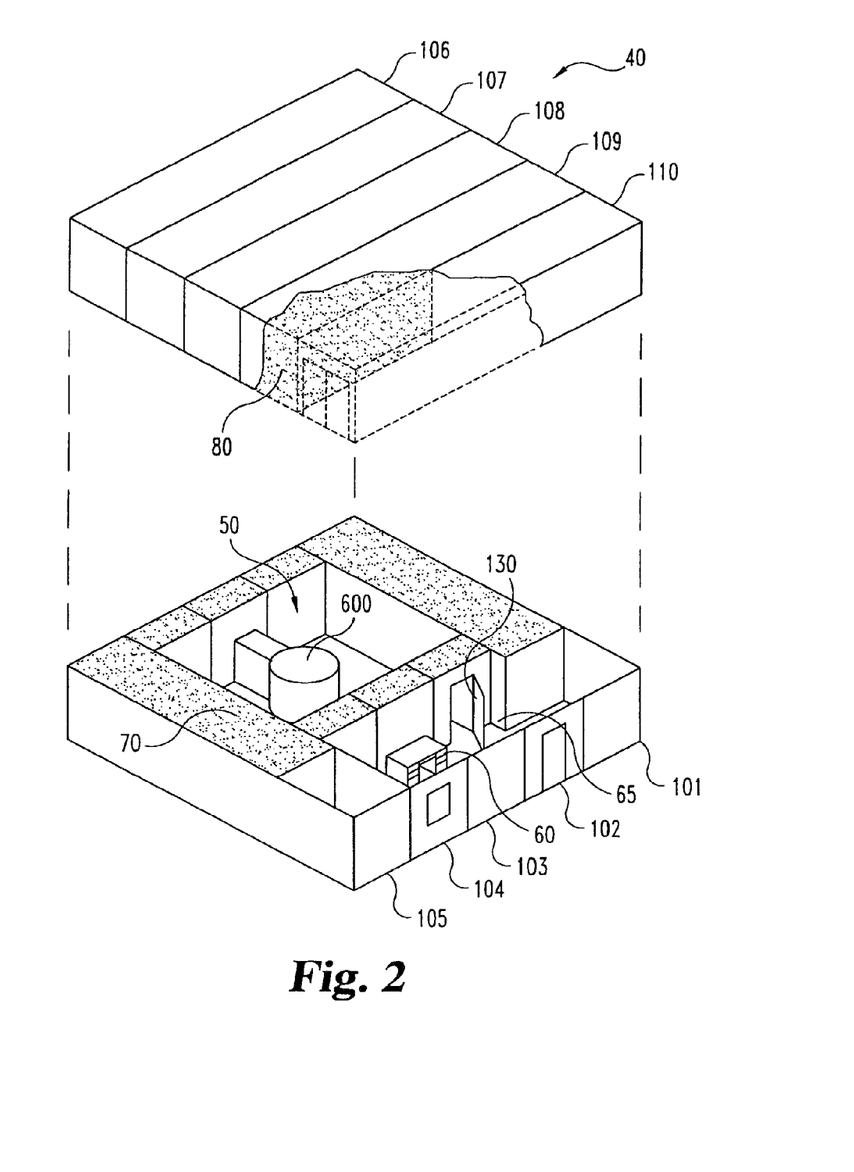
FIG. 2 is an exploded, perspective view in partial section of the modular structure of FIG. 1.

Turning now to FIGS. 1 and 2, structure 40 for housing therapeutic radiation equipment is depicted. Structure 40 is a modular unit that is assembled to form a radiation therapy vault room 50, and can be delivered to a site in sections with all equipment and finishings in place. The individual sections 101-110, herein referred to as pods or modules, are preferably each capable of being shipped by rail, ship, or overland freight and of being assembled together using commonly available equipment such as cranes or container movers. In addition, the pods are preferably built to meet the US Department of Transportation (DOT) regulations concerning travel on the interstate highways. Currently, the DOT code includes a weight limitation of 85,000 pounds including the tractor and the trailer along with size limitations of a width not exceeding 14 feet, a height not exceeding 13 feet 6 inches, and a length not exceeding 53 feet.

Referring now to FIGS. 1-4, as assembled, the modular structure 40 includes a total of ten pods and has two or more interior rooms. One room 50 is adapted to contain equipment capable of being used to perform radiation therapy, and the other room 60 is adapted to be used as a control area suitable for use by a radiation therapist operating the equipment contained in room 50. Either room 50 and/or room 60 can be further divided into additional rooms, for example to provide a patient waiting area or multiple treatment areas. The modular unit 40 also has a series of interior and adjoining containers that can be filled with radiation shield material to form a barrier 70 around the treatment area 50 and a roof barrier 80 above the treatment area 50. The radiation shield material can be a flowable and/or granular material such as sand.

Figure 3:
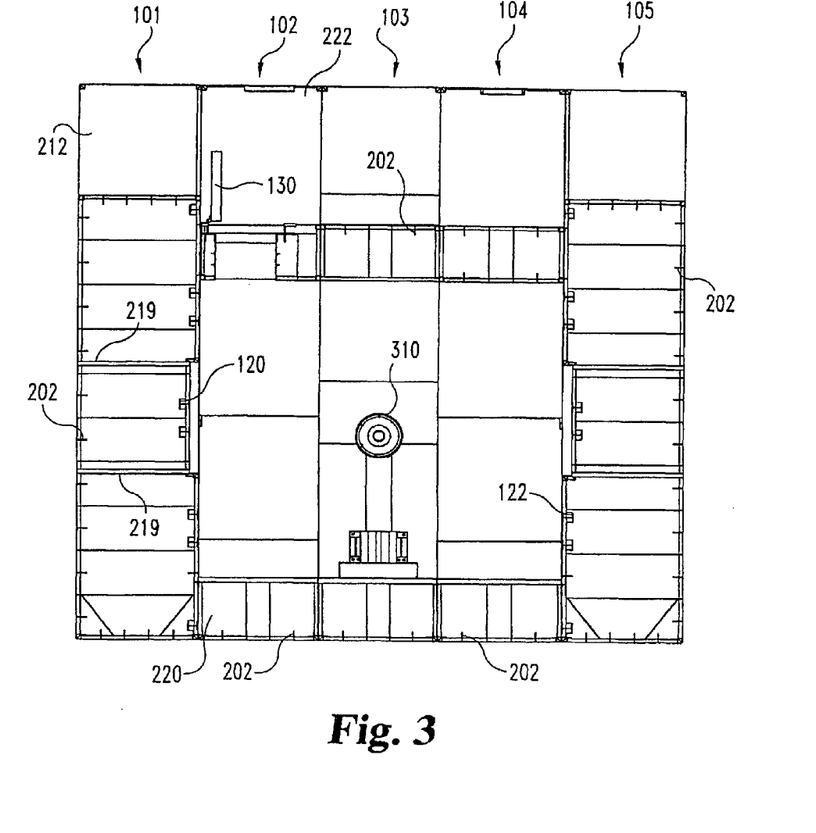
FIG. 3 is a top plan view of the first floor level of the structure of FIG. 1.

Five pods (pods 101-105 referred to as the footprint pods) are used to form the footprint of the building 40 (see FIG. 3). An additional five pods, (pods 106-110, referred to as the roof pods) are placed on top of and perpendicular to the five footprint pods (see FIG. 4). Of the five roof pods, four pods (pods 106-109, referred to as the "roof shielding pods") give additional radiation shielding in the vertical direction by way of the roof barrier 80, whereas pod 110 is primarily used as a storage area.

Pods 102, 103, and 104 connect together to form the interior workspace or therapy room 50. These pods align to form a continuous unobstructed space, for example a space measuring approximately 24 feet wide and 20 feet in length. Pod 103 serves as the center footprint pod, containing most of the medical equipment, and has quick connections for electrical power and a mounting platform for the medical equipment 600. A weather seal can be incorporated along the joints between all of the footprint pods as well.

Figure 4:
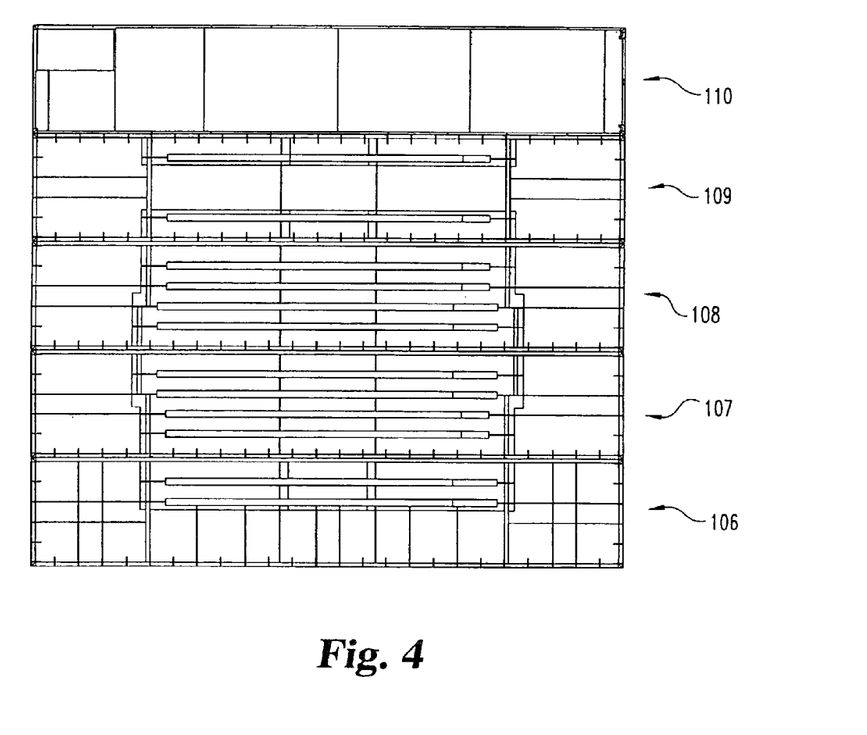
FIG. 4 is a top plan view of the second floor level of the structure of FIG. 1.

Pod 101 is attached to the exterior side of pod 102, and pod 105 is attached to the exterior side of pod 104. These two pods (pod 101 and pod 105), together with portions of pods 102-104, receive the radiation shielding material to form the barrier 70. The barrier 70 extends substantially around all sides of the room 50, with pod 102 including a doorway to permit access to the treatment room 50. The roof shielding pods (pods 106-109) are placed above and connected to the five footprint pods, at least pods 101 and 105 including roof support structures 120, 122 to support the load of the roof pods. Pods 106-109 are used for radiation shielding purposes whereas pod 110 can be reserved to house the electrical equipment, telephone equipment and other utilities.

For assembly a suitable foundation, such as a concrete slab, is first created. The foundation is then leveled and the first of the footprint pods, for example pod 103, is placed on and anchored to the foundation. The remaining footprint pods are then sequentially placed and attached to their respective adjoining pod(s) and to the foundation and a weather seal is formed between adjoining pods and the foundation. A portion of the radiation shielding material can then be pumped into the containers of the various footprint pods to form the barrier 70.

Either before or after filling the containers of the various footprint pods with the radiation shielding material, the roof pods can be placed on and attached to the five footprint pods. A weather seal can then be made between the footprint pods and the roof pods as well as between adjoining roof pods. The modular structure 40 can then be filled with the shielding material. Electrical, water and sewage are then connected to the modular unit. By providing the structure 40 as a modular unit, the assembly time from the pods' arrival on site to the finished structure 40 can be minimized. It is envisioned that the formation of the structure 40 would only take on the order of a few (3-4) days, greatly decreasing the time and cost traditionally needed to construct a radiation treatment facility.

Having described the general layout of the pods and the formation of the structure, more particular features of the individual pods are considered. Each of the pods can be built with an outside dimension generally the same as a standard eight by forty foot extended height (9'6") shipping container. The pods are transportable, which means that they each meet DOT regulations and codes for overland freight. Optionally, each can also be rigidly constructed to be capable of being lifted from the end points by a container mover. They can also be formed to be stacked five pods high, for example during transit in an ocean going vessel. The pods can also be constructed to be shipped and stacked with other container types where the other containers having a gross weight of 96,000 pounds each. The shipping weight of each pod, including any additional shielding or support structures or other integrated components, but without the radiation shielding fill material, is most preferably consistent with DOT shipping regulations for moving by truck without special permitting.

More particularly, each of the pods is constructed of a steel exterior skeleton or frame 90 (see FIG. 5) that generally defines the outer edges of the pod. The frame 90 is preferably formed of square channel and flat plate steel welded, bolted, or otherwise securely fastened together to form the boundaries of the generally rectangular solid shape of the pod. "C" shaped beams 92 form the longer lower sides of the rectangular footprint of each pod, with angled rails 96 forming the upper borders. Rectangular posts 94 form the four side edges between the upper 96 and lower 92 rails. Where present, wall segments are secured to the interior of the skeleton or frame 90 (for example by welds or rivets) with any wall or floor segments intended to contain the radiation fill material formed of flat sheet steel. Other wall, floor, or ceiling segments can be mounted to the frame and formed of any suitable building material. Where, a wall, floor, or ceiling segment is not present in any individual pod, or is of non-load bearing construction, structural rigidity of the pod can be increased to the desired level by providing rigid support members between segments of frame 90.

Figure 5:
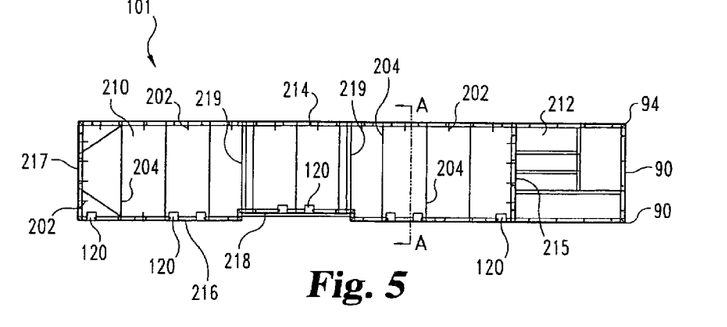
FIG. 5 is a top plan view of a first pod in the embodiment of FIGS. 3 and 4.

Turning now to FIG. 5, pod 101 is constructed in two regions, a fill area 210 and a finishable area 212. The fill area 210 forms a part of the barrier 70 and does not contain a floor so that the radiation shielding material provided into area 210 can be substantially continuous to the foundation. Area 210 also does not have a ceiling. The finishable area 212 has no side wall along the section that joins to pod 102, but a floor can be provided. The interior of area 212 can be suitable for interior finishing of the floors, wall and ceiling to make it a patient area.

Figure 5A:
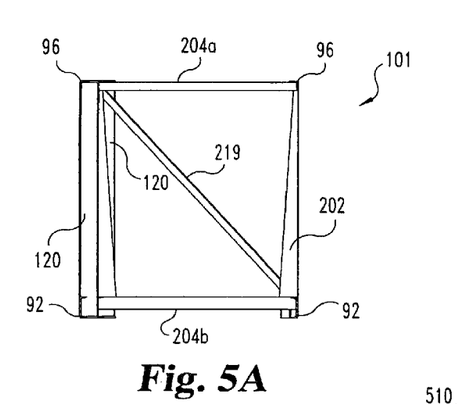
FIG. 5A is a side elevational view in full section of the FIG. 5 pod.
Figure 5B:
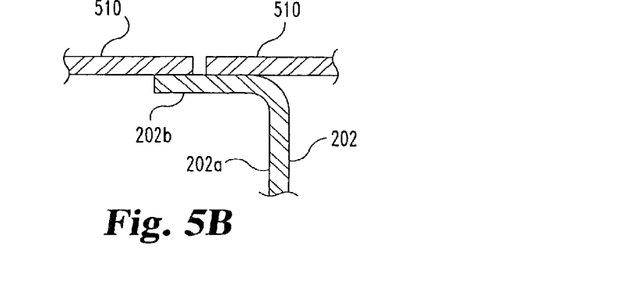
FIG. 5B is a partial enlarged top plan view in full section of adjacent wall segments and a wall support.

Fill area 210 is defined by oppositely disposed vertical inside and outside walls 214 and 216 and side walls 215 and 217. Optionally, inside wall 216 is at least partially absent at the portion that adjoins to the barrier regions of pod 102 to permit fill material to flow between the adjacent barrier regions. Each of the walls are rigid and can be reinforced to contain the load of the radiation fill material without substantial deflection. Each of the walls are constructed of flat panel steel and have a plurality of vertically oriented supports 202 welded or otherwise affixed thereto at spaced intervals along the wall length. Where more than one wall panel 510 is required to span the length of a wall, the supports 202 also serve to connect adjacent panels of the wall material. (See FIG. 5B) The supports are elongated pieces with a "L" shaped cross section having one flat portion 202b welded or riveted to adjacent steel wall sections 510 and a second flat portion 202a generally perpendicular to the wall panels 510. The perpendicular extending portions of supports 202 are tapered such that they are thicker at the bottom of the walls where the largest lateral force from the fill material can be expected. (See FIG. 5A)

For additional lateral support in the radiation fill area, rigid horizontal supports 204 are also affixed generally between the top portions (204a in FIG. 5A) and bottom portions (204b) of the walls, or equivalently directly to the frame structure 90. Steel supports 204 extend between walls 216 and 214 and at angles between wall 215 and walls 216 and 214 and between wall 217 and walls 214 and 216.

In typical use the lateral force on the walls of container 210 could be 170,000 pounds at a pressure of approximately 6.4 pounds per square inch. The maximum lateral force could be increased by the weight of the fill from the roof pods on the top of pod 101, and the wall material, thickness and supports should be chosen to support the load.

It is to be understood that the actual load and pressures experienced by the various portions of the pods might vary by a factor of 10 or more in either direction from any of the estimated loads presented herein. Among other things, these exemplary loads can be expected to depend on the density of the fill material. In addition, the walls and/or associated supports can be designed to withstand several times the expected load for any particular application.

In addition, access ports can be placed at appropriate intervals along the walls of container 210 to allow a pump or other suitable fill mechanism to fill and empty the container of the shielding material. Alternatively the fill portion 210 can be filled and emptied through its open top and bottom.

Pod 101 is constructed to include central region 218 in which additional shielding, such as a lead plate, may be added. Region 218 can be, for example, eight feet wide by 9.5 feet high and seven inches thick and located near the center of pod 101 or wherever relatively larger radiation levels could be expected (for example depending on the orientation and use of the medical device in room 50). A variety of shielding materials may be used for this purpose and they may be a passive or a structural part of the pod. Diagonally extending rigid lateral supports 219 are provided to accommodate any additional weight of the additional shielding material.

The roof shielding pods will be placed on top of pod 101 perpendicular to the footprint pods and filled with radiation shielding material. The weight of the filled roof shielding pods could be as high as 250,000 pounds each, all of which load can be substantially supported by pod 101 and pod 105. Pod 101 includes roof supports 120 as a portion of the wall to hold one half of the weight of the four roof shielding pods and transfer the weight to the foundation below. As discussed above, the majority of portion 210, like similar fill areas of the other footprint pods, has an open top to allow fluid communication with the roof pods.

Figure 6:
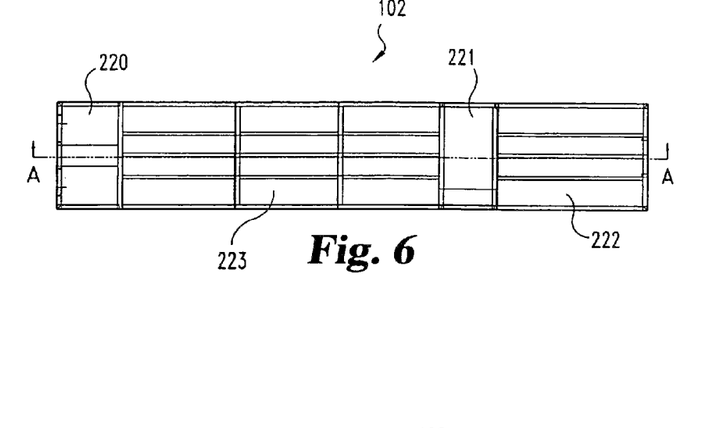
FIG. 6 is a top plan view of a second pod from the embodiment of FIGS. 3 and 4.
Figure 6A:
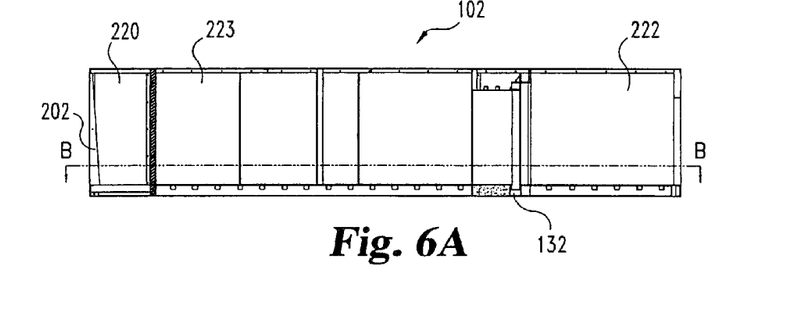
FIG. 6A is a side elevational view in full section of the FIG. 6 pod.
Figure 6B:
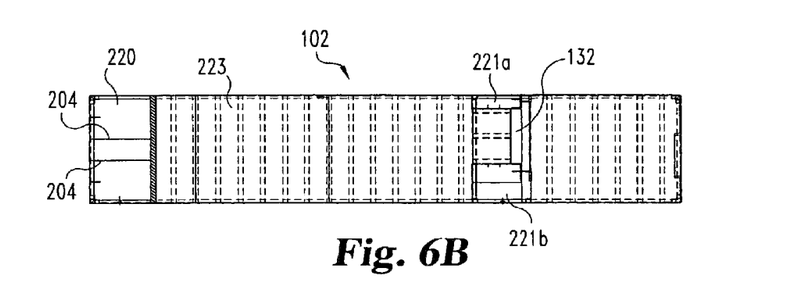
FIG. 6B is a top plan view in full section of the FIG. 6 pod.

Turning now to FIG. 6 and with continued reference to FIGS. 3 and 4, pod 102 is adjacent to pod 101. Pod 102 also has several regions within it. Region 220 is eight feet wide by six feet deep and the full height of the pod. It is located in the rear of the pod and forms a portion of the barrier 70. When filled with radiation shielding material the weight of the fill in portion 220 might be 44,0000 pounds with approximately 6.4 pounds per square inch of weight. Area 220 does not contain a floor or ceiling so that the shielding material can be substantially continuous to the foundation and to the roof barrier. The lateral force on the side walls might be 34,000 pounds, and the maximum lateral force could be increased by the weight of the fill from the roof shielding pods on the top of this pod. The wall material, thickness and supports should be chosen to support these exemplary loads or the load for any particular application.

Area 221 contains a vault door 130. Door 130 is five feet wide by seven and one half feet high. The door is a hollow steel door eight inches thick. The hollow portion of the door can be filled with four inches of lead, and 3.8 inches of boridated polyethylene. It is envisioned that the weight of the door with its frame and additional wall shielding adjacent to the frame will be approximately 10,000 pounds.

Door 130 is located between areas 221a and 221b that, like area 220, are adapted to receive the radiation fill material. Door 130 separates the control room 60, or patient area 65 (of which area 222 is a part) from the treatment room 50 allowing access back and forth. Area 222 also includes a standard exterior door consistent with local building codes to allow access to the patient area 65.

Portions 223 and 222 are suitable for interior finishing of the floors, walls and ceiling to make it a patient area. They can also have provision for a quick connect for electricity, for lighting and to operate the vault door 130.

Pod 102 also includes a door jam mechanism to be used for additional protection against radiation out leakage in the event there is no maze shielding walls (as is traditionally provided at the entrance to radiation rooms) or when the maze is not sufficient to adequately block radiation leakage. The mechanism includes a lifting mechanism coupled to a retractable threshold 132 that pops up to be adjacent to door 130 upon the closing of vault door 130, effectively blocking radiation leakage. The threshold 132 retracts, returning to its place upon the opening of the door. The lifting mechanism can include a pair of hydraulic cylinders 134, 136 (see FIGS. 14 and 14A) of the type known as pancake cylinders. A gear or lever assembly actuatable under the force of the closing door could also be used. The lifting mechanism (cylinders 134, 136) are electronically or hydraulically activated by a switch that senses whether the door is open or closed, for example by provision of a pair of cooperating magnetic sensors mounted on the door and door jam respectively. Preferably the threshold 132 is electronically interlocked with a pair of door switches and/or with the radiation machine 600 such that the machine 600 is prohibited from being in use when the door 130 or the threshold 132 are in a position to allow radiation leakage from the room.

Figure 14:
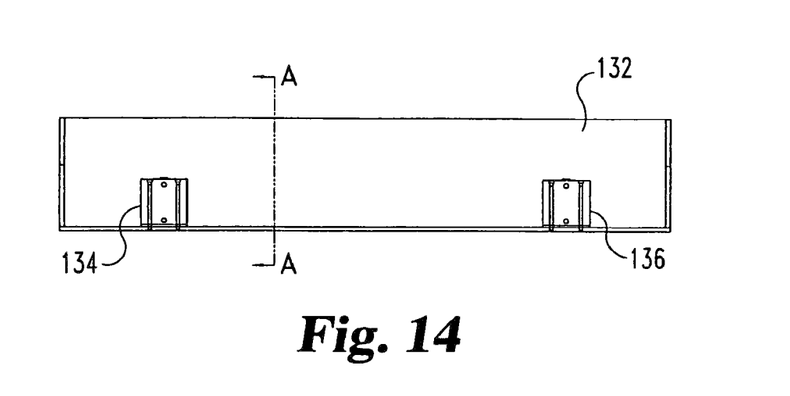
FIG. 14 is a front elevational view of the lifting mechanism for the retractable threshold.
Figure 14A:
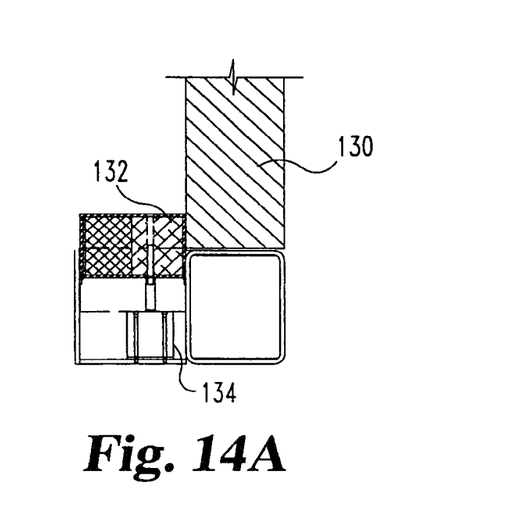
FIG. 14A is a side elevational view in full section of the threshold of FIG. 14 in the raised position adjacent the closed vault door.

The door jam is normally hidden and level with the floor so as not to be a hazard for persons walking across it. When the vault door 130 is closed, cylinders 134, 136 raise the threshold above the bottom of the door to block radiation leakage under the door. In the event of any emergency, the pop-up mechanism of the door jam can work in conjunction with the vault door and/or be actuated manually. For example, the door jam can require electrical power to stay in the raised position such that in the event of a power failure, the threshold 132 automatically retracts under its own weight. The door jam is an enhancement to any radiation therapy center, as most centers do not utilize any type of a seal under a vault door. The door jam is not restricted to the use of the modular system and can be retrofitted to any type of door as would occur to those of skill in the art when presented with the present disclosure.

Figure 7:
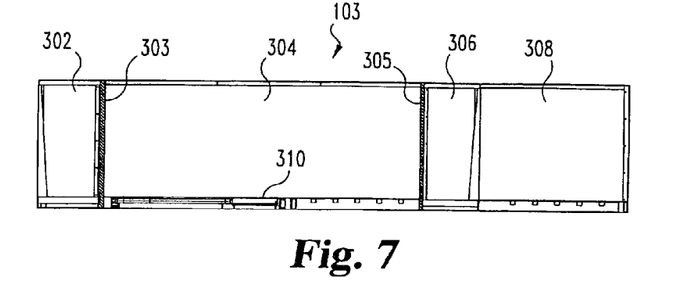
FIG. 7 is a side elevational view in full section of a third pod from the embodiment of FIGS. 3 and 4.

Pod 103 is located in between pod 102 and pod 104. It is to be built with an outside dimension the same as an eight by forty-foot extended height (9'6") shipping container. When finished, it can meet DOT regulations and codes and be capable of being lifted from the end points by a container mover.

As illustrated in FIG. 7, pod 103 is divided into four sections. Sections 302 and 306 are fill areas that do not contain a ceiling or a floor and are open to the fill areas of the adjacent pods. The lateral force on the side walls might be 34,000 pounds, where the maximum lateral force could be increased by the weight of the fill from the roof shielding pods on the top of this pod. The wall material, thickness and supports should be chosen to support this exemplary load or the load dictated by any particular application. Access ports can be placed at appropriate intervals to allow a vacuum pump to fill and empty the container of the shielding material.

Additional shielding panels 303 and 305 are added between areas 302 and 304 and between areas 304 and 306. Steel may be used for this purpose, and it may be a passive or a structural part of the pod.

There is no side wall on areas 304 and 308 adjacent to pods 102 or 104. Pod 103 is capable of being connected to pods 102 and 104 with a watertight weather seal and it has provisions to anchor it to the foundation in accordance with standard building codes for a mobile building. Areas 304 and 308 are suitable for interior finishing of the floors, walls and ceiling to make it a patient area.

Pod 103 is adapted to hold a medical treatment device, such as one containing a therapeutic radiation source. There are several manufacturers of such equipment, and the design of the structure and pod 103 in particular will be as universal as is economically possible to allow for the incorporation of as many different makes and models of the treatment device as possible. In general, the average machine weighs 18,000 pounds and bolts to a base plate such as base plate 310. The bolts that hold the machine are at one end of the machine and the bulk of the weight is at the other some ten feet forward of the bolts yielding a significant moment of torque. A steel base frame is incorporated into the steel frame of pod 103 to accommodate this torque. The frame is sufficiently rigid such that regardless of any bending or twisting during transit, when the frame of pod 103 is placed on a precision leveled foundation, the machine will be level to within the manufacturers specifications. Other electrical equipment including a control console, modulator rack, power transformers, and power filters can also be mounted within pod 103. Wiring conduits are built into the frame to service the electrical equipment.

Pod 104 is substantially a mirror image of pod 102 with a few minor exceptions. Pod 104 fits in between pods 103 and 105, and does not include a vault door. In addition, whereas portion 222 of pod 102 included an exterior door, the equivalent portion of pod 104 can include other amenities such as plumbing for a wash basin.

Pod 105 is substantially a mirror image of pod 101 although it is contemplated that the equivalent portion to portion 212 of pod 101 will be adapted for a different purpose, such as storage, restrooms, etc.

Figure 8:
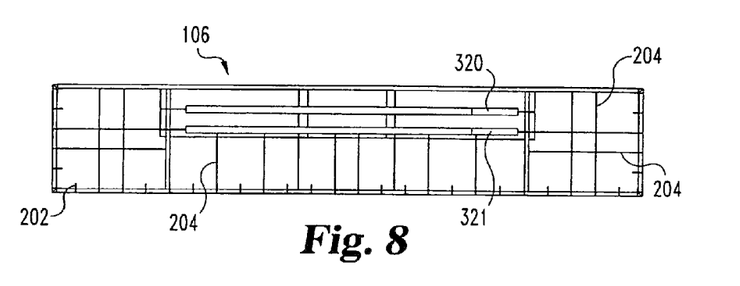
FIG. 8 is a top plan view of a sixth, second floor pod from FIG. 4.
Figure 8A:
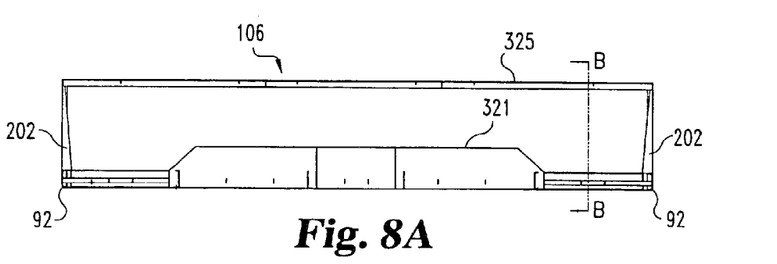
FIG. 8A is a side elevational view in full section of the FIG. 8 pod.
Figure 8B:
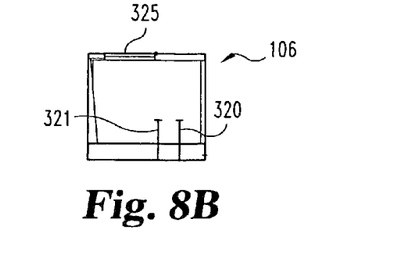
FIG. 8B is an end elevational view in full section of the FIG. 8 pod.

With reference to FIGS. 8 and 8B, pod 106 is one of four roof shielding containers to be placed on top of and perpendicular to footprint pods 101 through 105. Each of the roof shielding containers can be built with an outside dimension the same as a standard shipping container. Pod 106 is placed at the rear of the modular unit. The bottom of pod 106 attaches to the top of the footprint pods 101 through 105. The side of pod 106 that attaches to pod 107 does not have a wall, but it includes a central rigid support between the upper and lower frame segments. When finished it can meet DOT regulations and codes, and be capable of being lifted from the end points by a container mover. It can also be capable of being stacked five containers high with the other containers having a gross weight of 96,000 pounds each and be capable of being shipped with a gross weight of 96,000 pounds. The shipping weight of the pod with the additional shielding and the roof support structures but without the radiation shielding fill material is preferably consistent with DOT shipping regulation for moving by truck without special permitting.

As is the case for all of the roof pods, there is no floor in pod 106 in the area over pod 101 and pod 105 and over the shielding containers in pods 102, 103 and 104 although there is a steel floor over the treatment room portions of the footprint pods. In addition, there is a ceiling or roof covering all of pod 106 (as is also the case for all the roof pods). When filled with radiation shielding material the total weight of the fill could be 243,200 pounds with approximately 5.3 pounds per square inch of weight on both the shielding in the lower pods and on the floor in the existing areas of this pod. The lateral force on the side walls could be 115,520 pounds. The lateral force could be approximately 5.3 pounds per square inch occurring near the bottom of the pod. The wall material and thickness and supports should chosen to support this exemplary load or any particular load depending on the application. Access ports can be placed at appropriate intervals to allow a vacuum pump to fill and empty the container of the shielding material. In particular, access ports 325 can be provided along the roof as a series of spaced apart holes with normally closed spring loaded covering flaps through which access to the interior space of the roof pods can be selectively provided.

Pod 106 is supported by the four steel supports 120 in pods 101 and 105. It is constructed to span pods 102, 103 and 104 without bowing or placing any undue stress on these three pods, and includes a pair of I-beams 320, 321 to distribute the load on the steel floor to supports 120.

Pod 107 is another of four roof shielding containers to be placed on top of and perpendicular to the footprint pods 101 through 105. It is placed in front of and adjacent to pod 106 at the rear of the modular unit. The bottom of pod 107 attaches to the top of footprint pods 101 through 105. The side of pod 107 that attaches to pod 108 also does not have a wall, which helps to minimize gaps and/or radiation leaks through the roof. Pod 107 attaches to the five footprint pods and to pod 106 and 108. There will be no floor in pod 107 in the area over pod 101 and pod 105. When filled with radiation shielding material the total weight of the fill could be 243,200 pounds with approximately 5.3 pounds per square inch of weight on both the shielding in the lower pods and on the floor in the existing areas of this pod. The lateral force on the side walls could be approximately 115,520 pounds. The wall material and thickness and supports should be chosen to support this exemplary load or the particular load as determined by the application. Access ports are placed at appropriate intervals to allow a vacuum pump to fill and empty the container of the shielding material.

Pod 107 is supported by the supports 120 in pods 101 and 105. It is be constructed to span pods 102, 103 and 104 without bowing or placing any undue stress on these three pods, and includes four I-beams to span pods 102 though 104 and distribute the load to the supports 120.

Pod 108 is one of four roof shielding containers to be placed on top of and perpendicular to the footprint pods 101 through 105. It is placed in front of and adjacent to pod 107 near the center of the modular unit. The bottom of pod 108 will attach to the top of footprint pods 101 through 105. One side of pod 108 will attach to pod 107 and the other side will attach to pod 109. There is no floor in pod 108 in the area over pod 101 and pod 105. When filled with radiation shielding material the total weight of the fill could be 243,200 pounds with approximately 5.3 pounds per square inch of weight on both the shielding in the lower pods and on the floor in the existing areas of this pod. The lateral force on the side walls could be 115,520 pounds. As discussed above with respect to the other pods, the wall material and thickness and supports should be chosen to support this exemplary load. Access ports can also be placed at appropriate intervals to allow a vacuum pump to fill and empty the container of the shielding material.

Pod 108 is supported by the supports 120 in pods 101 and 105. It is be constructed to span pods 102, 103 and 104 without bowing or placing any undue stress on these three pods, and includes four I-beams to span pods 102 though 104 and distribute the load to the supports 120.

Figure 9:
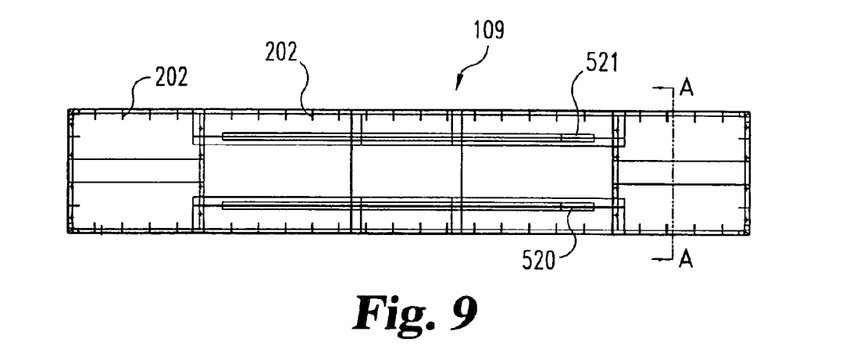
FIG. 9 is a top plan view of a ninth, second floor pod.
Figure 9A:
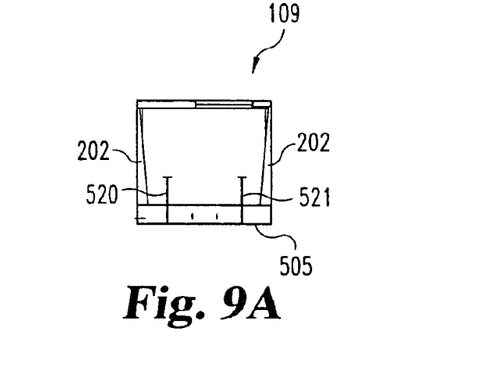
FIG. 9A is an end elevational view in full section of the FIG. 9 pod.

With reference to FIGS. 9 and 9A, pod 109 is one of four roof shielding containers to be placed on top of and perpendicular to the footprint pods 101 through 105. It will be placed in front of and adjacent to pod 108 near the center of the unit. The bottom 505 of pod 109 will attach to the top of footprint pods 101 through 105. There is no floor in pod 109 in the area over pod 101 and pod 105 and over the shielding containers in pods 102, 103 and 104. When filled with radiation shielding material the total weight of the fill could be 243,200 pounds with approximately 5.3 pounds per square inch of weight on both the shielding in the lower pods and on the floor in the existing areas of this pod. The lateral force on the side walls could be 115,520 pounds. As described above with respect to the other pods, the wall material and thickness and supports should be chosen to support this exemplary load. Access ports can also be placed at appropriate intervals to allow a vacuum pump to fill and empty the container of the shielding material.

Pod 109 is supported by the supports 120 in pods 101 and 105. It is be constructed to span pods 102, 103 and 104 without bowing or placing any undue stress on these three pods, and includes I-beams 520, 521 to span pods 102 though 104 and distribute the load to the supports 120.

Pod 110 is a utility area that will be one of the five roof pods. Pod 110 will be placed on top of and perpendicular to pods 101 through 105. Pod 110 will have several rooms built into it. These rooms will be for utility areas and will be built to be consistent with local building codes for electrical, telephone, plumbing and other utilities as required.

It is envisioned that pod 110 could also be supported by supports placed in pods 101 and 105. However, it is envisioned that since pod 110 would not contain the radiation fill material, the load of pod 110 would be substantially less than the load of any of pods 106 through 109 and thus can be supported in any conventional fashion.

In one variation of the modular structure the medical device can be removed and replaced after the structure is completed in a simple and efficient manner. This variation involves modifications to pods 103 and 109 such that the portion of pod 103 containing the medical device and any associated control system can be removed and replaced while the remainder of the structure and the majority of the radiation fill material remains in place.

Figure 10:
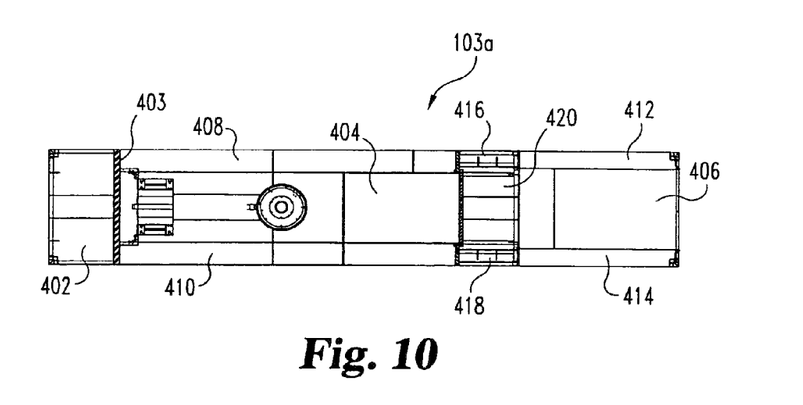
FIG. 10 is a top plan view in full section of an alternative arrangement for a third pod in the embodiment of FIGS. 3 and 4.
Figure 11:
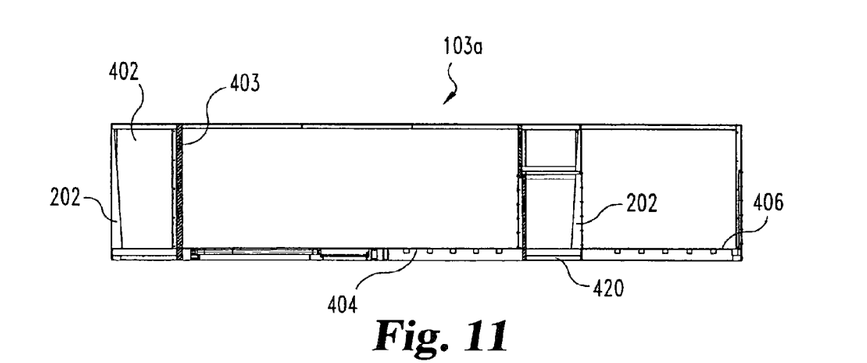
FIG. 11 is a side elevational view in full section of the FIG. 10 pod.

Turning now to FIGS. 10 and 11, pod 103*a*, which is a modified version of pod 103, is depicted. Pod 103*a* includes radiation fill section 402 that is separated from the radiation treatment room 50 by lead shield 403. The removable portion of pod 103*a* includes the treatment room portion 404, barrier portion 420 and control room portion 406. The treatment room portion 404 includes the base plate that would be coupled to the medical device and is removable with respect to treatment room portions 410 and 408. The control room portion 406 includes the associated control equipment and electronics and is electrically coupled to and integral with portions 420 and 404.

The barrier comprising portions 416, 418 and 420 in pod 103*a* can be filled with radiation shielding fill material. Portions 416 and 418 are relatively fixed and would normally remain filled with shielding material even during the medical device interchange operation. The center barrier portion 420 is part of the removable section of pod 103*a* and can be evacuated of its radiation fill material as necessary to remove and replace the medical device. The walls of radiation fill portions 416 and 418 abutting portion 420 are reinforced to contain the load of fill material when portion 420 is evacuated.

The associated electronic controls for the medical device are included on portion 406, which is adapted to be slid out between portions 412 and 414. While each of sections 404, 420 and 416 are preferably coupled together, they could be separately removable. In addition rollers or other slide assisting means are preferably provided under the removable sections so that the removable section of pod 103*a* can easily be decoupled and removed and replaced.

Figure 12:
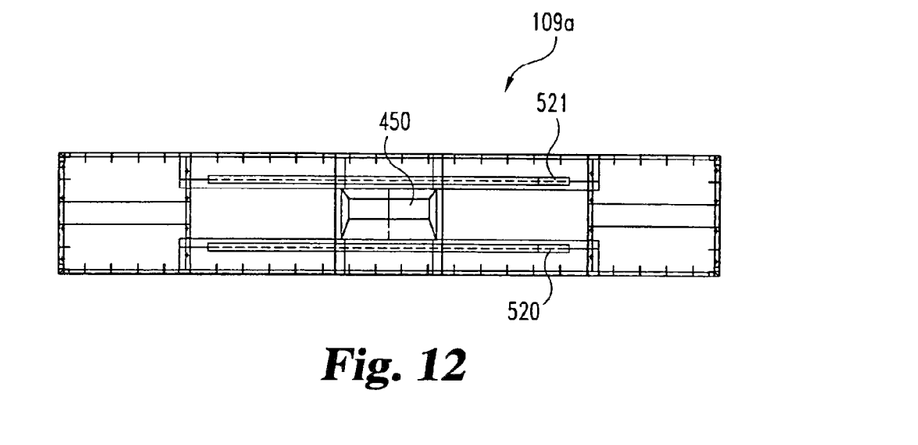
FIG. 12 is a top plan view of an alternative arrangement for a ninth, roof pod in the embodiments of FIGS. 3 and 4.
Figure 13:
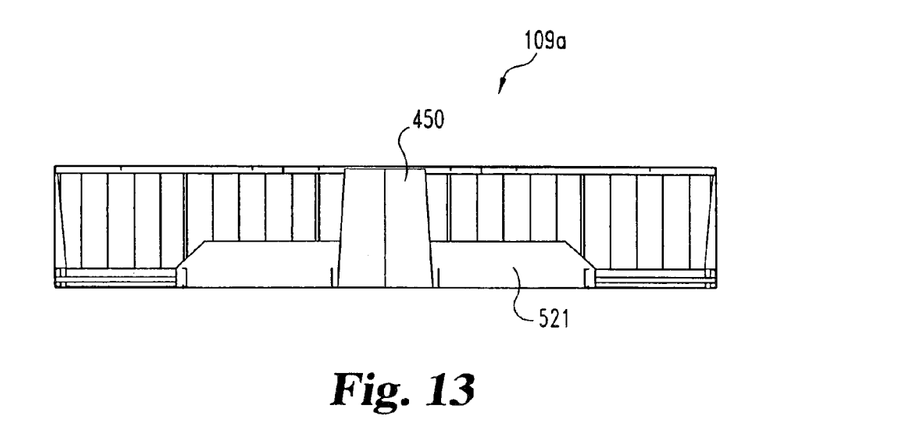
FIG. 13 is a side elevational view in full section of the FIG. 12 pod.

In addition provisions can be made to stop the flow of fill material from the roof sections above portion 420 as the removable portion of pod 103*a* are removed. Turning now to FIGS. 12 and 13, pod 109*a*, which is a modified version of pod 109, is depicted. Pod 109*a* is substantially identical to pod 109 save the centralized trapezoidal portion 450 which is located to cover portion 420 in pod 103*a*. Portion 450 is constructed of reinforced steel and has access ports to both fill and evacuate portion 450 of radiation fill material when removable section of pod 103*a* is to be removed. The lateral sides of portion 450 are constructed to contain the load of the remaining radiation fill material in pod 109*a* from falling into portion 420 during medical device removal and swapping.

As can be appreciated by those of skill in the art when provided with the present disclosure, the modular structure can be formed by sequentially placing and connecting the pods in proper alignment. To facilitate construction and alignment of the pods, adjacent pods can be provided with quick locking and/or aligning devices and/or the pods can be connected in any conventional fashion. For example adjacent sides of two pods can be provided with a post and receiving hole to align with the respective post or receiving hole of the adjacent pod.

Figure 15A:
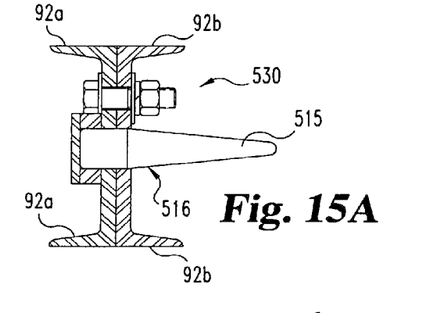
FIG. 15A is an end elevational view in partial section of a representative connection between the lower rails forming the long sides of adjacent pods.

Turning now to FIG. 15A, a representative connection between the lower rails 92 of a pair of footprint pods is illustrated. Alignment post 515 of rail 92*a* is received in the hole 516 of rail 92*b*, and the two rails are secured by a bolt and locking washer assembly 530.

Figure 15B:
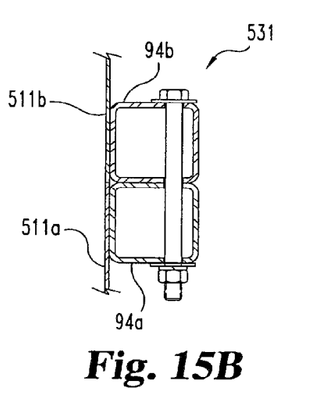
FIG. 15B is a top plan view in partial section of a representation connection between the corner posts of adjacent pods.

Turning to FIG. 15B, a representative connection between the vertical posts 94 at the corners of adjacent pods is illustrated. Post 94*b*, including wall section 511*b*, is connected with long bolt assembly 531 to post 94*a*, including adjacent wall section 511*a*.

Figure 15C:
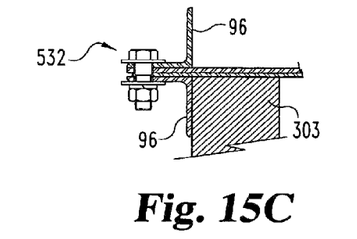
FIG. 15C is a top plan view in partial section of a representative connection between interior wall segments of adjacent pods.

Turning now to FIG. 15C, an interior wall connection between adjacent pods is illustrated. Adjoining rails 96, or equivalently wall supports 202, are connected by bolt assembly 532. One or more of the rails 96 can include a reinforced wall portions, such as wall 303. (See FIG. 7)

Figure 15D:
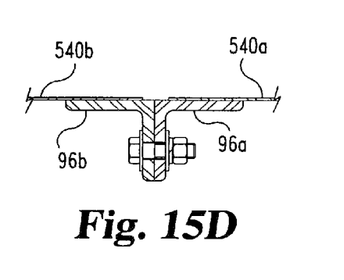
FIG. 15D is an end elevational view in partial section of an upper rail connection between adjacent pods.

As shown in FIG. 15D, the rails 96*a* and *b* (of adjacent pods) holding ceiling panels 540*a* and *b* are connected in similar fashion as are adjacent interior wall portions. The ceiling panels 540*a* and 540*b* could be the ceiling over the central treatment area 50, or the ceiling panels could serve as the roof over the entire structure, as would be the case in the respective connection between pods 106 and 107.

Figure 15E:
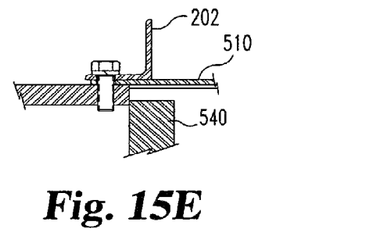
FIG. 15E is a top plan view in partial section of an adjacent pod connection to a door gusset portion of a pod.

Turning to FIG. 15E, a representative connection between an interior portion of pod 101 with the door gusset 540 of pod 102 is illustrated. A representative wall panel 510, reinforced with support 202, is secured to a portion of the door gusset 540 with a standard bolt assembly.

Figure 15F:
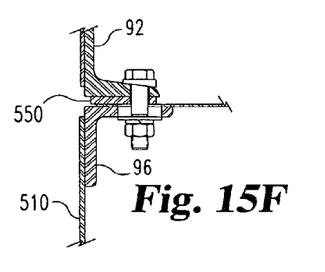
FIG. 15F is a side elevational view in partial section of a representative connection between an end of a roof pod with the outer wall and frame of a footprint pod.

Turning now to FIG. 15F, a representative connection between the ends of a roof pod with the outside walls of pods 101 and 105 is depicted. The upper frame rail 96 from the outside wall 510 of a footprint pod receives a bolt assembly holding the lower beam 92 forming the bottom of a roof pod, such as pod 107. A spacer 550 can also be included between the pods.

Figure 15G:
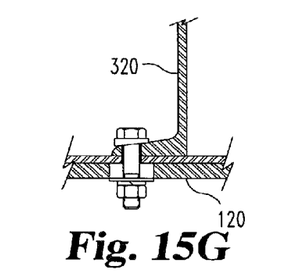
FIG. 15G is a side elevational view in partial section of a representative connection of the load support beams in the roof pods with the roof support structures in the footprint pods.

Turning now to FIG. 15G, a representative connection between an I-beam in the roof pod and the roof support in the footprint pod is depicted. I-beam 321 (see FIG. 8-8B) is connected through the floor of the roof pod and into a top flat portion of the support 120 (see FIG. 3) with a bolt assembly.

In addition while each radiation fill material containing section of each of the individual pods can include their own access port or ports for filling and removing radiation fill material, in one embodiment only the roof pods have access ports. In this embodiment the access ports can be along the top roof section of the roof pods and radiation fill material provided into those roof pods can flow by gravity into the appropriate portions of the footprint pods 101 through 105.

It is also envisioned that the modular structure can be disassembled by sequentially decoupling and removing the pods. For the roof pods, the radiation fill material can be pumped out of or otherwise removed from the containers prior to lifting the pods. The footprint pods, since there is no floor in the barrier sections, can be lifted by their ends with the filler material being left behind. It may be necessary to rap the sides of the pods as they are being lifted to assure that the filler does not stick to the inside of the pods. Alternatively, the filler material can be pumped out of the footprint pods prior to their removal.

While in the preferred embodiment, the radiation shielding filler material is sand or another solid flowable or granular radiation adsorbent material, other types of filler material can be used. Examples include, without limitation, silica, dirt, lead, lead shot, steel, scrap pieces (such as metal punch outs), and various combinations or mixtures of the above. Where the barrier region is made substantially fluid tight such as by providing a bladder and/or caulking throughout the barrier region once the pods are constructed, the filler material can be a liquid (such as water) or a slurry (such as a flowable fill concrete). Furthermore, it is contemplated that the specific type of shielding material and the physical dimension of the barrier region can be together varied and selected to provide the necessary radiation shielding based on a particular application and a particular radiation source. As discussed throughout, the density of the fill material will determine at least to some extent the load on the walls of the barrier, and the walls can be constructed and/or reinforced as appropriate based on the expected load and any applicable building codes or construction techniques.

While the structure illustrated herein is constructed substantially entirely from free-standing pods, it is contemplated that the pods could only form a portion of a treatment facility. For example pods 102 and/or 103 could be provided wherein the remainder of the structure and/or the barrier (i.e. that formed in the illustrated embodiment by the remainder of the pods) could be constructed by any building technique now known or hereafter developed. For example portions of the structure could be transported as preformed but collapsed portions that would be assembled and arranged around the placed pods.

It is to be understood that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A method for constructing a radiation treatment facility, comprising:
    providing a foundation for the facility;
    providing a first free-standing module including a horizontally elongated support frame structure and a base plate;
    lifting the first module and then moving the lifted first module over the foundation and then lowering the first module onto the foundation;
    providing a first opening in an exterior side of the first module so as to allow construction of a patient treatment room encompassing an area inside the first module and an area outside the first module;
    wherein the treatment room includes radiation emitting equipment suitable for use in performing radiation therapy on a patient coupled to the base plate; and
    wherein constructing the patient treatment room includes placing a second module adjacent the first opening in the exterior side of the first module.

2. The method of claim 1 wherein constructing the patient treatment room includes placing a third module adjacent a second opening in an exterior side of the first module.

3. The method of claim 1 wherein the radiation emitting equipment is bolted to the base plate.

4. The method of claim 3 wherein the radiation emitting equipment has a center of mass that is substantially offset from the bolts connecting the radiation emitting equipment to the base plate so as to yield a moment of torque that is accommodated by the support frame structure.

5. The method of claim 1 wherein the first module is lifted with a container mover.

* * * * *